(12) United States Patent
Serata et al.

(10) Patent No.: US 7,321,060 B2
(45) Date of Patent: Jan. 22, 2008

(54) METHOD FOR PRODUCTION OF ACRYLIC ACID

(75) Inventors: Naoki Serata, Himeji (JP); Kouji Ueno, Himeji (JP); Harunori Hirao, Himeji (JP); Takeshi Yokogoshiya, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 10/858,974

(22) Filed: Jun. 2, 2004

(65) Prior Publication Data

US 2004/0249200 A1 Dec. 9, 2004

(30) Foreign Application Priority Data

Jun. 5, 2003 (JP) ............................. 2003-160770

(51) Int. Cl.
*C07C 51/42* (2006.01)
*C07C 51/16* (2006.01)

(52) U.S. Cl. .................. 562/600; 562/532; 562/545

(58) Field of Classification Search ........... 562/512, 562/523, 531, 532, 542, 544, 598
See application file for complete search history.

(56) References Cited

U.S. PATENT DOCUMENTS

| | | | |
|---|---|---|---|
| 5,315,037 A | | 5/1994 | Sakamoto et al. |
| 5,785,821 A | * | 7/1998 | Sakamoto et al. ............ 203/57 |
| 5,817,865 A | | 10/1998 | Machhammer et al. |
| 5,910,607 A | * | 6/1999 | Sakakura et al. ........... 562/532 |
| 6,384,274 B1 | | 5/2002 | Elder et al. |
| 6,482,981 B2 | | 11/2002 | Ueno et al. |
| 6,540,881 B1 | | 4/2003 | Sakamoto et al. |
| 6,599,397 B2 | | 7/2003 | Sakamoto et al. |
| 6,713,648 B2 | | 3/2004 | Hirao et al. |
| 2003/0028052 A1 | * | 2/2003 | Hirao et al. ................ 562/600 |
| 2004/0249200 A1 | | 12/2004 | Sereta et al. ................ 562/545 |

FOREIGN PATENT DOCUMENTS

| | | | |
|---|---|---|---|
| JP | 1993246941 | * | 1/1993 |
| JP | 2001-348359 | | 12/2001 |
| JP | 2004359614 | | 12/2004 |

OTHER PUBLICATIONS

Office Action issued Feb. 16, 2007 for the corresponding Chinese Patent Application No. 200410063128.9; Applicant: Nippon Shokubai Co., Ltd.; Application Date: Jun. 4, 2004.

* cited by examiner

*Primary Examiner*—Karl Puttlitz
(74) *Attorney, Agent, or Firm*—Mathews, Shepherd, McKay & Bruneau, P.A.

(57) ABSTRACT

A method for the production of acrylic acid of high concentration by absorbing acrylic acid with high absorption ratio of acrylic acid is provided. In a method for producing acrylic acid by a procedure comprising a step of catalytic gas phase oxidation reaction and a step of absorbing the acrylic acid-containing gas, while a low boiling substance-containing solution is introduced into the absorption column via a portion different from the top of the column.

7 Claims, 1 Drawing Sheet

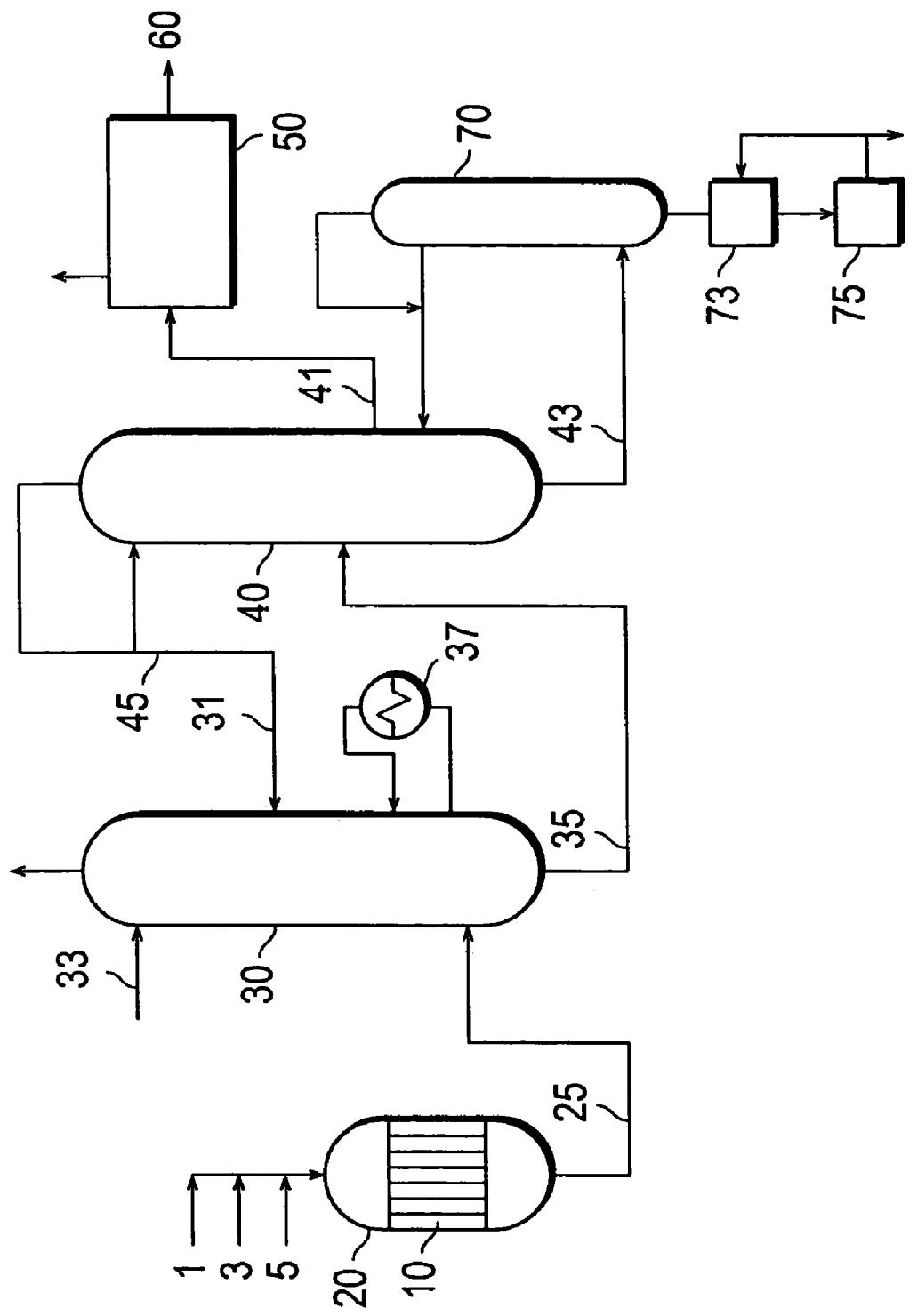
FIGURE

METHOD FOR PRODUCTION OF ACRYLIC ACID

BACKGROUND OF THE INVENTION

1. Field of the Invention

This invention relates to a method for the production of acrylic acid which, at a step of absorbing acrylic acid, enhances the absorption ratio of acrylic acid by introducing a low boiling substance-containing solution through a portion different from the top of an absorption column.

2. Description of the Related Art

Commercial production of acrylic acid generally resorts to the method of propylene oxidation which consists in subjecting propylene and/or acrolein to catalytic gas phase oxidation. When acrylic acid is produced by this method of propylene oxidation, the step of propylene oxidation gives rise to such impurities as water, acids like propionic acid, acetic acid, and maleic acid, and aldehydes like acetone, acrolein, furfural, and formaldehyde in the form of by-products. The gas containing these by-products is absorbed as an acrylic acid-containing solution generally via contact with an absorbent. This solution is subsequently purified by separating the absorbent by such a means as distillation and further separating low boiling substances and high boiling substances. The minute amount of such impurities as aldehydes which cannot be easily separated by distillation is possibly purified by a chemical treatment or a process of crystallization. However, the purification to a high degree necessitates many steps and complicates equipment and operation and forms one cause for degrading the yield of acrylic acid.

One known method, for example, produces acrylic acid of high purity by absorbing an acrylic acid-containing gas resulting from catalytic gas phase oxidation with a high boiling solvent, distilling the acrylic acid-containing solution thereby separating it into the solvent and crude acrylic acid, and subsequently subjecting the crude acrylic acid to a process of crystallization (JP-A-1997-227445). This method, however, forms a complicated procedure which comprises a step of cooling an acrylic acid-containing gas with a venturi, and then a step of absorbing the cooled gas and subsequently a step of removing low boiling substance, and thereafter a step of separating a high boiling solvent and crude acrylic acid by a distillation column.

If the step of acrylic acid production is enabled to treat the acrylic acid-containing solution of high concentration, it will enjoy the efficiency of decreasing the amount of treatment at the subsequent step of purification. Thus, one known method comprises supplying a reaction composition containing more than 7 vol % of propylene, molecular oxygen, and steam and the balance of an inert gas to a reaction vessel having disposed therein numerous reaction tubes each formed of two reaction zones packed with a catalyst thereby utilizing a propylene reactant of high concentration (JP-A-2000-103761). In a working example 2 cited in the official gazette, the absorption with water obtained an acrylic acid-containing solution having an average concentration of 73.8 wt %.

Another method has been disclosed which comprises introducing an acrylic acid-containing gas into an absorption column, introducing a recovery water containing acetic acid emanating from the bottom liquid of a solvent recovering column at the purifying step into the top of the absorption column thereby effecting absorption of acrylic acid therein, and producing as the bottom liquid of the absorption column an acrylic acid-containing solution composed of 50-80 wt % of acrylic acid, 2-5 wt % of acetic acid, and the balance of water (JP-A-1993-246941). This method obtains purified acrylic acid by subjecting the acrylic acid-containing solution to azeotropic dehydration using a mixed solution of two or more azeotropic solvents and subsequently passing the product of dehydration through such steps as the removal of high boiling substance.

Still another method has been disclosed which, in the absorption with water of an acrylic acid-containing gas resulting from a reaction of catalytic gas phase oxidation, comprises supplying the recovery water emanating from the step of azeotropic dehydration to the absorption column, supplying the resultant acrylic acid-containing solution to a stripping column, and obtaining an acrylic acid solution composed of 70.9 wt. % of acrylic acid, 25.6 wt. % of water, and 2.0 wt. % of acetic acid via the bottom of the stripping column (JP-A-2001-199931). This method obtains purified acrylic acid by performing azeotropic dehydration of the acrylic acid-containing solution and subsequently subjecting the product of dehydration to the step of crystallization.

The method disclosed in the official gazette mentioned above, however, is such that when an organic solvent is used as the absorbing solvent, this method necessitates a subsequent step of separating the solvent. In spite of this addition to the process, the method does not deserve to be regarded as producing the acrylic acid-containing solution of sufficiently high concentration. An attempt to obtain in the bottom liquid of the absorption column an aqueous acrylic acid solution containing acrylic acid in high concentration results in lowering the absorption efficiency and proves commercially infeasible. Such is the true state of affairs.

Thus, it is an object of this invention to provide a method for producing acrylic acid in high concentration by absorbing acrylic acid at high yield.

And, it is an object of this invention to provide a method for producing acrylic acid of high purity at a high yield by a simple process from the acrylic acid-containing solution mentioned above as the raw material.

SUMMARY OF THE INVENTION

The present inventor has found that an acrylic acid-containing solution of high concentration is obtained by supplying a low boiling substance-containing solution (excluding water as a low boiling substance) through a portion different from the top of the absorption column in addition to the absorbing aqueous solution used at the step of absorbing acrylic acid with water and that, at the purifying step using the acrylic acid-containing solution of such high concentration, the treatment of dehydration can be performed without using an azeotropic solvent. This invention has been perfected as a result. To be specific, this invention provides a method for producing acrylic acid by a procedure comprising a step of obtaining an acrylic acid-containing gas by subjecting propylene and/or acrolein to the reaction of catalytic gas phase oxidation and a step of obtaining an acrylic acid-containing solution by absorbing the acrylic acid-containing gas with an absorbing aqueous solution, wherein a low boiling substance-containing solution (excluding water as a low boiling substance) to a portion different from the top of the acrylic acid-absorption column. By introducing the low boiling substance-containing solution (excluding water as a low boiling substance) to the portion different from the top of the absorption column, it is made possible to enhance the absorption efficiency of acrylic acid more than the method which is made to the top of the column. As a result, the acrylic acid-containing solution of high concentration can be prepared as the bottom liquid of the absorption column and the solution can be treated for dehydration without using an azeotropic solvent. Since no azeotropic solvent is used, the installation of a step of azeotropic dehydration, a step of recovering the solvent, and a step of oil-water separation can be omitted and the acrylic acid can be produced by a simple process. Further, as the low boiling substance-containing solution of this nature (excluding water as a low boiling substance), the solutions discharged at the subsequent steps may be used.

BRIEF DESCRIPTION OF THE DRAWING

FIG. 1 is a process diagram illustrating one example of the preferred mode of embodying this invention.

DESCRIPTION OF THE PREFERRED EMBODIMENT

This invention concerns a method for producing acrylic acid by a procedure comprising a step of subjecting propylene and/or acrolein to the reaction of catalytic gas phase oxidation thereby obtaining an acrylic acid-containing gas and a step of absorbing the acrylic acid-containing gas with the absorbing aqueous solution and obtaining an acrylic acid-containing solution, characterized by introducing a low boiling substance-containing solution (excluding water as a low boiling substance) to a portion different from the top of the acrylic acid absorption column.

In this invention, the term "different from the top" refers to the number of theoretical plate in the range of 2-100 (2≧, 100≦) where the column top is assumed to have the number of theoretical plate of 1 and the column bottom the number of theoretical plate of 100. The term "purification" embraces distillation, stripping, crystallization, extraction, absorption, partial condensation, and the like. Here, the term "distillation" is supposed to mean a method of separating a volatile component contained in the solution by heating this solution to the boiling point thereof, the term "stripping (in distillation)" a method of supplying a stripping gas in a distillation column and transferring a target subject in the liquid phase into the gas phase, the term "crystallization" a method of separating a target substance by crystallization from the liquid phase and the gas phase, the term "extraction" a method of separating a target substance by dissolution into a solvent, the term "absorption" a method of separating a target substance in the gas phase or the liquid phase by contact with a liquid or a solid, and the term "partial condensation" a method of separating a target substance by condensing part of a gas or a steam. The term "low boiling substance" as used in this invention refers to a substance having a boiling point lower than acrylic acid in the normal state and the term "high boiling substance" to a substance having a boiling point higher than acrylic acid in the normal state. The term "low boiling substance-containing solution (excluding water as a low boiling substance)" introduced to a portion different from the top of the acrylic acid absorption column means a solution containing low boiling substances excluding water. It will be referred to simply as "low boiling substance-containing solution." Now, this invention will be described below with reference to The FIGURE which illustrates one example of the preferred mode of embodying this invention.

This invention obtains an acrylic acid-containing gas 25 by supplying propylene and/or acrolein 1, a molecular oxygen-containing gas 3, and a diluting gas 5 to a reaction vessel 20 incorporating a catalyst 10 for catalytic gas phase oxidation. This gas 25 is supplied to the bottom of an absorption column 30 which has a low boiling substance-containing solution 31 supplied thereto via the intermediate stage thereof and the absorbing aqueous solution 33 is supplied to the absorption column via the top thereof to establish contact between the acrylic acid-containing gas 25 and the absorbing aqueous solution 33. As the low boiling substance-containing solution, a distillate 45 emanating from a first distillation column 40 which will be specifically described herein below may be used wholly or partly. An acrylic acid-containing solution 35 which forms the bottom liquid of the absorption column may be cooled in a cooling device 37 and then circulated to the absorption column 30. Consequently, an acrylic acid-containing solution 35 which contains acrylic acid in high concentration is obtained. Next, the acrylic acid-containing solution 35 is supplied to the first distillation column 40 and deprived of low boiling substances like water contained therein to obtain crude acrylic acid 41. Acrylic acid 60 as a finished product is obtained by supplying the crude acrylic acid 41 to a crystallizing device 41. Since the high boiling substances contained in bottom liquid 43 of the first distillation column 40 contain acrylic acid dimer, they are supplied to a second distillation column 70 provided in the bottom thereof with a thin film vaporizing device 73 to induce concentration of acrylic acid dimer. Then, the dimer is retained in a dimer decomposing tank 75 and thermally decomposed therein into acrylic acid. This acrylic acid is returned to the thin film vaporizing device 73 and further circulated via the second distillation column 70 to the first distillation column 40 and/or the absorption column 30 so as to be recovered as a finished product. When the air contains a water component, it is preferred to be dehumidified before it is supplied to the reaction vessel. The reason for this dehumidification is that the amount of the water component introduced into the reaction vessel and consequently the amount of the water component introduced into the absorption column can be decreased by the dehumidification.

In this invention, propylene and/or acrolein can be used as the raw material gas of acrylic acid. While the reaction vessel 20 does not need to be particularly restricted but is only required to be capable of performing a reaction of catalytic gas phase oxidation. The shell-and-tube type reaction vessel can be used advantageously in respect that it excels in the efficiency of reaction. By packing the reaction vessel 20 with the well-known catalyst 10 for catalytic gas phase oxidation and then bringing the raw material gas into contact with such a molecular oxygen-containing gas 3 as oxygen or air, it is made possible to effect the oxidation of the raw material gas. When propylene is used as the raw material gas, the propylene concentration is in the range of 7-15 vol % and water concentration is in the range of 0-10 vol % and the molecular oxygen concentration is such that the ratio of propylene:oxygen (by volume) falls in the range of 1:1.0-2.0. Air may be used as the source of supply of molecular oxygen. If necessary, oxygen rich gas and pure oxygen can be used as the souse of supply of molecular oxygen. As concrete examples of the diluting gas 5, nitrogen, carbon dioxide, and other inert gases may be cited. Optionally, the gas discharged via the top of the absorption column 30 may be used.

The reaction of catalytic gas phase oxidation performed by using propylene as the raw material is generally carried out in two stages by the use of two kinds of catalyst 10 for catalytic gas phase oxidation. The catalyst for the first stage of this reaction is capable of forming acrolein mainly by the gas phase oxidation of the raw material gas containing propylene in a gas phase and the catalyst for the second stage of the reaction is capable of forming acrylic acid mainly by the gas phase oxidation of the raw material containing acrolein. As the catalyst for the first stage of the reaction, a complex oxide containing iron, molybdenum, and bismuth may be cited. As the catalyst for the second stage of the reaction, a catalyst having vanadium as an essential component may be cited.

The FIGURE depicts the mode of performing the two-stage reaction mentioned above with a single reactor. Optionally, these reactions may be performed in a tandem system having two different reaction vessels connected to each other. The acrylic acid-containing gas 25 which is obtained by the reaction of catalytic gas phase oxidation contains 5-14 vol % of acrylic acid, 0.1-2.5 vol % of acetic acid, 0.5-3.0 vol % of molecular oxygen, and 5-36 vol % of water and other components which are unaltered component of the raw material gas and by-products of reaction such as propionic acid, maleic acid, acetone, acrolein, furfural, formaldehyde and $CO_x$.

In the acrylic acid absorption column 30, any of the known methods of contact may be used for establishing contact between the acrylic acid-containing gas 25 and the absorbing aqueous solution 33. As concrete examples of such methods of contact, crossflow contact devices using a bubble-cap tray, a uniflat tray, a perforated tray, a jet tray, a valve tray, and a venturi tray; and counter current contact devices using a turbo-grid tray, a dual flow tray, a ripple tray, a kittel tray, gauze type, sheet type, and grid type structured packings and random packings may be cited.

This invention is characterized by absorbing acrylic acid while supplying the low boiling substance-containing solution 31 to the intermediate stage of the absorption column 30 during the absorption of acrylic acid by virtue of the contact between the acrylic acid-containing gas 25 and the absorbing aqueous solution 33. The acrylic acid is absorbed by the absorbing aqueous solution 33 which falls from the top of the column. During this absorption, low boiling substances excluding water such as, for example, acetic acid are introduced via a portion different from the top of an absorption column because their introduction results in enhancing the absorption ratio of acrylic acid. Though the mechanism of this enhancement remains yet to be clarified, it may be logically explained by a supposition that the introduction of acetic acid via a certain site of the absorption column 30 results in adding to the layer of acetic acid gas occupying the neighborhood of the position for supply of acetic acid, inducing changes in affinity and pressure relation, changing the gas distribution inside the absorption column so as to form a layer of lower boiling substance gas above the acetic acid layer and a layer of higher boiling substance gas below it, and transferring acrylic acid toward the bottom of the column. It is particularly advisable to effect the introduction of the acetic acid-containing solution from the position of the number of theoretical plate of not less than 2, preferably the number of theoretical plate of not less than (the amount of the number of theoretical plate of the absorption column× 0.25), and particularly the number of theoretical plate of not less than (the amount of the number of theoretical plate of the absorption column×0.5) as counted from the top of the column. At the top of the column, the increase of the acetic acid gas layer brings only a minute effect of enhancing the absorption efficiency of acrylic acid and rather results in degrading the absorption efficiency of acrylic acid.

Incidentally, this effect is not limited to acetic acid. The low boiling substance is only required to be different from water. The same effect is observed when a compound having a boiling point not exceeding 141° C., preferably falling in the range of 60-141° C., and particularly preferably in the range of 100.5-141° C. in the normal state. As concrete examples of the low boiling substance which is introduced into the acrylic acid absorption column via a portion different from the top of the column in this invention, acetic acid, formic acid, propionic acid, and acrolein may be cited. These compounds at the step of acrylic acid production can be expelled via the top of the absorption column 30 and the top of the first distillation column 40 similarly to other low boiling substances.

The concentration of the low boiling substance contained in the low boiling substance-containing solution may be properly selected to suit the amount of introduction. It falls generally in the range of 2-100 wt. %, preferably in the range of 5-100 wt. %, particularly in the range of 5-60 wt. %, and further particularly in the range of 5-50 wt. %. If this concentration falls short of 2 wt. %, the shortage will result in lowring the effect of varying the gas phase distribution inside the absorption column mentioned above. When a plurality of low boiling substances are contained in the low boiling substance-containing solution, the total of their amounts is used for the relevant computations.

Further in this invention, the low boiling substance-containing solution to be used contains the low boiling substance of the aforementioned concentration and the weight ratio of the low boiling substance in the low boiling substance-containing solution to the acrylic acid-containing gas is set at a mass flow rate 0.005-0.20 times, preferably 0.008-0.15 times, and particularly preferably 0.01-0.10 times the mass flow rate of acrylic acid contained in the acrylic acid-containing gas. If this mass flow rate falls short of 0.005 times, the shortage will result in disrupting the effect of enhancing the absorption efficiency of acrylic acid. Conversely, if the ratio exceeds 0.20 times, the excess will result in compelling part of the introduced low boiling substance to be expelled via the bottom of the column and rendering the acquisition of the acrylic acid-containing solution of high concentration difficult.

In this invention, as the low boiling substance-containing solution 31 of the nature mentioned above, the distillate of the distillation column which issues from the step of acrylic acid purification may be used. The distillate 45 emanating via the top of the first distillation column 40 which will be specifically described herein below is an example. Acetic acid, formic acid, propionic acid, and acrolein which are low boiling substances are separated together with water as the distillate of the low boiling substance separation column from acrylic acid. When the conditions of distillation of the first distillation column 40 and the conditions of separation of low boiling substance are coordinated, the distillate emanating via the top of the distillation column 40 contains acetic acid, formic acid, propionic acid, acrolein, water, and acrylic acid and constitute the aforementioned low boiling substance-containing solution. Thus, the low boiling substance-containing solution can be prepared without requiring new addition of low boiling substances into the system.

As the absorbing aqueous solution 33 to be used in this invention, a wide variety of aqueous solutions which are only required to be capable of absorbing acrylic acid are available. The temperature of the absorbing aqueous solution to be introduced into the column falls in the range of 0-60° C., preferably in the range of 10-55° C., and particularly in the range of 20-50° C.

The weight ratio of the absorbing aqueous solution mentioned above to the acrylic acid-containing gas is set at a mass flow rate not less than 0.1 times, preferably 0.15-2.0 times, and particularly 0.2-1.5 times the mass flow rate of acrylic acid contained in the acrylic acid-containing gas. It is advisable to effect the absorption of acrylic acid by causing this absorbing aqueous solution and the acrylic acid-containing gas to come into counter current contact. If the mass flow rate falls short of 0.1 times, the shortage will possibly result in inducing an extreme decrease in the efficiency of the acrylic acid absorption column. The absorbing aqueous solution may incorporate therein, for the purpose of preventing such polymerizing substances as acrylic acid from undergoing polymerization, one or more compounds selected from the group consisting of N-oxyl compounds, phenol compounds, manganese salts such as manganese acetate, copper salts of dialkyldithiocarbamic acid such as copper dibutylthiocarbamate, nitroso compounds, amine compounds, and phenothiazine which are cited in JP-A-2001-348360, 2001-348358, and 2001-348359.

Generally, the top of the acrylic acid absorption column is operated under pressure exceeding the normal pressure. In this invention, the absorption ratio of acrylic acid is enhanced by introducing the low boiling substance-containing solution via a portion different from the top of the column. The conditions of this absorption are varied by the amount of the low boiling substance-containing solution to be introduced, the concentration of the low boiling substance, the concentration of acrylic acid in the acrylic acid-containing gas, and the target concentration of acrylic acid in the acrylic acid-containing solution. In this invention, the column top pressure (gauge pressure) falls in the range of 0-0.4 MPa, preferably in the range of 0-0.1 MP, and particularly in the range of 0-0.03 MP. If the pressure falls short of 0 MPa (gauge pressure), the shortage will result in necessitating a decompressing device and requiring a cost of equipment and a cost of utilities. Conversely, if the pressure exceeds 0.4 MP, the excess will possibly require the temperature of the absorption column to be heightened considerably for the purpose of permitting extraction of such low boiling substances as water and acetic acid via the top of the column and result in lowering the absorption efficiency. The column top temperature falls generally in the range of 30-85° C. and particularly in the range of 40-80° C. In this invention, it is under these conditions of absorption that the acrylic acid-containing solution 35 containing 70-98 wt. % of acrylic acid, 0.1-5.0 wt. % of acetic acid, 1.9-30 wt. % of water, and 0.01-5.0 wt. % of other impurities (acids such as maleic acid and propionic acid, and aldehydes such as furfural and formaldehyde) is obtained.

The acrylic acid-containing solution may be subjected to a treatment of distillation in the distillation column and it may be subjected to a step of acrolein separation prior to the step of distillation mentioned above.

The separation column does not need to be particularly restricted but is only required to be capable of separating acrolein. A packed column or a plate column (tray column) may be used. The conditions of operating the separation column may be properly selected from among those used for the method of distillation or stripping, depending on the concentration of acrylic acid and the concentration of acrolein to be contained. In the case of distillation, the column top pressure (absolute pressure) falls in the range of 20-800 hPa, preferably in the range of 40-600 hPa, and particularly in the range of 60-400 hPa. If this pressure falls short of 20 hPa, the shortage will be at a disadvantage in requiring the column, condenser, and vacuum device to be enlarged and necessitating an expense of equipment. Conversely, if the pressure exceeds 800 hPa (absolute pressure), the excess will be at a disadvantage in heightening the temperature inside the separation column and exalting the possibility of polymerization. The column top temperature falls generally in the range of 30-100° C. and particularly in the range of 40-80° C. The bottom temperature of the column is 40-110° C., particularly 50-90° C. in general. Even in the case of stripping, the acrylic acid solution having the amount of contained acrolein decreased can be obtained by any of the hitherto known methods. The distillate emanating via the top of the column at the step of acrolein separation is estimated to contain acrolein only in a small amount. It has no effect of decreasing the acrylic acid loss and cannot constitute the low boiling substance-containing solution contemplated by this invention.

In this invention, the method of purifying the acrylic acid-containing solution 35 or the acrylic acid-containing solution resulting from the separation of acrolein does no need to be particularly restricted. The acrylic acid-containing solution 35, for example, may be supplied to the first distillation column 40 so as to separate crude acrylic acid containing substantially no water as a column bottom stream and/or a column side stream.

The first distillation column 40 does not need to be particularly restricted but is only required to be capable of separating acrylic acid. A packed column, a plate column (tray column), etc. are available, for example.

The first distillation column 40 can execute expected distillation under the conditions that enable such low boiling substances as water and acetic acid to be separated. This distillation does not require use of an azeotropic solvent. This is because a step of absorption produces an acrylic acid-containing solution of high concentration and, as a result, such low boiling-substances as water and acetic acid which are contained in the solution are efficiently separated as a distillate from the top of the first distillation column 40 without using an azeotropic solvent. Since no azeotropic solvent is used, the distillate mentioned above can be used as a low boiling substance containing aqueous solution without requiring oil-water separation. That is, the condition is preferable to select so that the distillate from the first distillation column 40 can be used as a low boiling substance containing solution, and acrylic acid can be separated from low boiling substance and high boiling substance. The conditions of the distillation may be properly selected, depending on the concentration of acrylic acid in the acrylic acid-containing solution 35 to be introduced and the purity of the crude acrylic acid aimed at. Commendably, the column top pressure (absolute pressure) is set in the range of 20-400 hPa, preferably in the range of 30 hPa-300 hPa, and particularly in the range of 30-200 hPa. If this pressure falls short of 20 hPa (absolute pressure), the shortage will be at a disadvantage in requiring the column, condenser, and vacuum device to be enlarged and the cost of equipment to be unduly increased. Conversely, if the pressure exceeds 400 hPa (absolute pressure), the excess will be at a disadvantage in heightening the temperature inside the distillation column 40 and adding to the possibility of polymerization. The column top temperature falls generally in the range of 30-70° C. and particularly in the range of 40-60° C. Then, the column bottom temperature falls generally in the range of 70-120° C. and particularly in the range of 80-110° C. The distillation performed under these conditions produces crude acrylic acid containing substantially no water and having an acetic acid content in the range of 0-1.0 wt. % as a column side stream of the distillation column.

In this invention, the purification of this crude acrylic acid may be executed by utilizing a step of azeotropic dehydration, a step of separating low boiling substances subsequent to the dehydrating step mentioned above, a step of separating high boiling substances, and other steps of purification which are disclosed in the official gazettes of JP-A-2000-290221, 2001-226320, 2001-348360, and 2001-348358 in addition to a distillation column illustrated as the first distillation column 40 in The FIGURE. This invention, however, is characterized by preparing an acrylic acid-containing solution of high concentration and purifying this solution and, as a result, enabling such low boiling substances as water and acetic acid to be removed from the solution without requiring use of an azeotropic solvent and avoiding installation of a solvent recovering column and an oil-water separating device for separating a solvent and a recovered water. Incidentally, the step of purifying acrylic acid does not need to be limited to purification by distillation. Optionally, the purification of acrylic acid may be effected by properly combining stripping, crystallization, extraction, absorption, and partial condensation.

This invention obtains the purified acrylic acid 60 by supplying the crude acrylic acid 41 to the crystallizing column 50. This mode of operation can be performed by following the procedure disclosed in JP-A-2001-199931 with necessary modifications.

The bottom liquid of the second distillation column 70 have high viscosity. The distillation column 70, therefore, is preferred to be provided additionally on the column bottom side with the thin film vaporizing device 73. Commendably, the second distillation column 70 executes the expected distillation with the number of theoretical plate in the range of 1-5 under a reduced pressure in the range of 10-150 hPa (absolute pressure) at a column bottom temperature of not higher than 120° C. The high boiling substances contained in the bottom liquid of the first distillation column 40 include acrylic acid dimer, maleic acid, and polymerization inhibitor, for example.

In this invention, acrylic acid may be distilled from the top of the second distillation column 40 and part of the distillate may be supplied to any of the crystallizing device 50, the first distillation column 40, and the absorption column 30.

The bottom liquid formed in the thin film vaporizing device 73 mentioned above is supplied to the dimer decomposing tank 75. In this dimer decomposing tank 75, the acrylic acid dimer is decomposed at a temperature in the range of 120-220° C. The hold up time (capacity of the dimer decomposing tank/amount of waste oil), though variable with the temperature of thermal decomposition, generally falls in the range of 20-50 hours. Optionally, the dimer decomposing tank may effect the decomposition in the presence of a catalyst such as sodium acrylate. After the acrylic acid dimer is decomposed into acrylic acid, the acrylic acid can be effectively utilized by circulating the acrylic acid to the thin film vaporizing device 73 and supplying the distillate from the top of the second distillation column 70 to the first distillation column 40. In this invention, the acrylic acid-containing solution of high concentration can be prepared in the acrylic acid absorption column 30, which solution can be prevented from polymerization by the addition of a polymerization inhibitor. At the step of absorption and the step of purification, the polymerization inhibitor is used in amounts proportional to the relevant concentrations of acrylic acid. In this invention, these polymerization inhibitors are expelled out of the system as a waste liquid of the dimer decomposing tank 75 to allow manufacture of acrylic acid 60 of high concentration as a finished product.

Incidentally, the residual mother liquid recovered from the crystallizing device 50 may be supplied in the whole amount to any of the absorption column 30, the first distillation column 40, the second distillation column 70, the thin film vaporizing devise 73, and the dimmer decomposing tank 75. Otherwise, part of the mother liquid may be discharged as waste oil to the out side of system. When the whole amount of the residual liquid mentioned above is supplied to the acrylic acid dimer decomposing step, part of the acrylic acid recovered from the acrylic acid dimer decomposing step may be discharged to the out side of system for the purpose of avoiding concentration of low boiling substances. Otherwise, the acrylic acid may be subjected to a chemical pretreatment for the purpose of converting aldehydes and maleic acid to high boiling substances before it is supplied to the acrylic acid dimer decomposing step. As a result, the concentration of impurities in the acrylic acid to be recovered by the acrylic acid dimer decomposing step can be decreased. This mode of operation may be carried out by following the procedure disclosed in JP-A-2001-199931 with necessary modifications.

The acrylic acid-containing solution or the acrylic acid-containing solution from which the low boiling substance has been separated and removed may be subjected to the aforementioned treatment of crystallization instead of undergoing the treatment of distillation in the first distillation column, despite deviation from the process illustrated in The FIGURE. The mother liquid of crystallization which is obtained at the step of crystallization as described above contains 2-15 wt. % of acetic acid. This invention allows the mother liquid of crystallization to be used as a low boiling substance-containing solution. By introducing the mother liquid of crystallization into the absorption column via a portion different from the top of the column, it is made possible to enhance the absorption efficiency of acrylic acid and prepare an acrylic acid-containing solution of high concentration.

EXAMPLES

Now, this invention will be described more specifically below with reference to working examples.

Example 1

By subjecting propylene to catalytic gas phase oxidation with a molecular oxygen gas in the presence of an oxidizing catalyst, a mixed gas containing 7.1 vol % of acrylic acid, 11.0 vol % of water, 81.3 vol % of inert gas, and 0.7 vol % of other substance was obtained at a rate of 17.2 kmol per hour.

This mixed gas was supplied at 168.1° C. to the bottom of an absorption column having the number of theoretical plate of 21 found by computation. With the pressure in the top of the column kept at 10.8 kPa, the column was operated while purified water containing a polymerization inhibitor as an absorbent was introduced via the top of the column at a rate of 31.6 kg per hour. At this time, the acrylic acid-containing solution was extracted via the bottom of the absorption column while the temperature of the top of the column was adjusted so as to cause the solution to have an acrylic acid concentration of 90 wt. %. The solution thus withdrawn was transferred to a distillation column.

When a liquid containing 15.0 wt. % of acrylic acid, 34.0 wt. % of acetic acid, and 51.0 wt. % of water was introduced at a rate of 10.50 kg per hour via the intermediate stage (the number of theoretical plate of 14 found by computation) into the absorption column, the temperature at the top of the absorption column reached 63.5° C., a gas was discharged at a rate of 17.7 kmol per hour via the top of the absorption column, and the amount of acrylic acid contained in the gas was 1.77 kg per hour.

Example 2

When an operation was performed by following the procedure of Example 1 while changing the site of introduction of the liquid into the absorption column to the number of theoretical plate of 5 found by computation, the temperature of the top of the absorption column reached 63.5° C., a gas was discharged at a rate of 17.7 kmol per hour via the top of the absorption column, and the amount of acrylic acid contained in the gas was 2.25 kg per hour.

Example 3

When an operation was performed by following the procedure of Example 1 while changing the site of introduction of the liquid into the absorption column to the bottom (the number of theoretical plate of 21 found by computation), the temperature of the top of the absorption column reached 63.5° C., a gas was discharged at a rate of 17.7 kmol per hour via the top of the absorption column, and the amount of acrylic acid contained in the gas was 1.88 kg per hour.

Comparative Example 1

When an operation was performed by following the procedure of Example 1 while changing the site of introduction of the liquid into the absorption column to the top (the number of theoretical plate of 1 found by computation), the temperature of the top of the absorption column reached 63.6° C., a gas was discharged at a rate of 17.7 kmol per hour via the top of the absorption column, and the amount of acrylic acid contained in the gas was 3.08 kg per hour.

Comparative Example 2

When an operation was performed by following the procedure of Example 1 while changing the liquid to be introduced into the absorption column so as to contain 15.0 wt. % of acrylic acid and 85.0 wt. % of water and no acetic acid, the temperature of the top of the absorption column reached 64.0° C., a gas was discharged at a rate of 17.9 kmol per hour via the top of the absorption column, and the amount of acrylic acid contained in the gas was 3.14 kg per hour.

Example 4

When an operation was performed by following the procedure of Example 1 while changing the liquid to be introduced into the absorption column so as to contain 15.0 wt. % of acrylic acid, 5.0 wt. % of acetic acid, and 80.0 wt. % of water, the temperature of the top of the absorption column reached 63.9° C., a gas was discharged at a rate of 17.8 kmol per hour via the top of the absorption column, and the amount of acrylic acid contained in the gas was 2.87 kg per hour.

Example 5

When an operation was performed by following the procedure of Example 1 while changing the liquid to be introduced into the absorption column so as to contain 15.0 wt. % of acrylic acid, 15.0 wt % of acetic acid, and 70.0 wt. % of water, the temperature of the top of the absorption column reached 63.8° C., a gas was discharged at a rate of 17.8 kmol per hour via the top of the absorption column, and the amount of acrylic acid contained in the gas was 2.42 kg per hour.

Example 6

When an operation was performed by following the procedure of Example 1 while changing the liquid to be introduced into the absorption column so as to contain 58.3 wt. % of acrylic acid, 20.0 wt. % of acetic acid, and 21.7 wt. % of water as a distillate from the top of the distillation column and changing the site of introduction of the liquid into the absorption column to the number of theoretical plate of 19 found by computation, the temperature of the top of the absorption column reached 62.3° C., a gas was discharged at a rate of 17.5 kmol per hour via the top of the absorption column, and the amount of acrylic acid contained in the gas was 1.68 kg per hour.

The invention claimed is:

1. A method for producing acrylic acid by a procedure comprising a step of subjecting propylene and/or acrolein to the reaction of catalytic gas phase oxidation thereby obtaining an acrylic acid-containing gas and a step of absorbing said acrylic acid-containing gas with an absorbing aqueous solution and obtaining an acrylic acid-containing solution, wherein a low boiling substance-containing solution (excluding water as a low boiling substance) is introduced into an acrylic acid absorption column at a site of a number of theoretical plates of not less than the amount of the number of theoretical plate of the absorption column times 0.5 as counted from the top of the column.

2. A method according to claim 1, wherein the concentration of the low boiling substance in the low boiling substance-containing solution is in the range of 2-100 wt. %.

3. A method according to claim 1, further comprising a step of purification of the acrylic acid-containing solution obtained by the absorbing step, where said low boiling substance-containing solution is a solution obtained from a step of purification.

4. A method according claim 1, wherein said low boiling substance is acetic acid.

5. A method according to claim 1, wherein said low boiling substance-containing solution has a boiling point in the range of 60-141° C. in the normal state.

6. A method according to claim 1, wherein the concentration of the low boiling substance in the low boiling substance-containing solution is in the range of 5-10%.

7. A method according to claim 1, wherein the weight ratio of the low boiling substance in the low boiling substance-containing solution to the acrylic acid-containing gas is set at a mass flow rate of 0.005-0.20 times the mass flow rate of acrylic acid contained in the acrylic acid-containing gas.

* * * * *